United States Patent
Kaufmann et al.

(10) Patent No.: US 12,005,032 B2
(45) Date of Patent: Jun. 11, 2024

(54) ELECTRONIC PILL BOTTLE TAG

(71) Applicant: Helios Center of Engineering Excellence, LLC, Sarasota, FL (US)

(72) Inventors: Jonathan Kaufmann, Shavano Park, TX (US); Benjamin Kaufmann, Shavano Park, TX (US); Nicholas Kaufmann, Shavano Park, TX (US); Doug Conyers, San Antonio, TX (US)

(73) Assignee: Helios Center of Engineering Excellence, LLC, Sarasota, FL (US)

( * ) Notice: Subject to any disclaimer, the term of this patent is extended or adjusted under 35 U.S.C. 154(b) by 820 days.

(21) Appl. No.: 17/101,956

(22) Filed: Nov. 23, 2020

(65) Prior Publication Data

US 2021/0154103 A1    May 27, 2021

Related U.S. Application Data

(60) Provisional application No. 62/938,757, filed on Nov. 21, 2019.

(51) Int. Cl.
| | |
|---|---|
| *G08B 21/00* | (2006.01) |
| *A61J 1/03* | (2023.01) |
| *A61J 1/14* | (2023.01) |
| *A61J 7/04* | (2006.01) |
| *G16H 20/13* | (2018.01) |

(52) U.S. Cl.
CPC .............. *A61J 7/0481* (2013.01); *A61J 1/03* (2013.01); *A61J 1/1412* (2013.01); *G16H 20/13* (2018.01); *A61J 2200/70* (2013.01); *A61J 2205/10* (2013.01)

(58) Field of Classification Search
CPC .......... A61J 7/0481; A61J 1/03; A61J 1/1412; A61J 2200/70; A61J 2205/10; A61J 7/049; A61J 7/0418; A61J 2200/30; G16H 20/13; B65D 41/0471; G06K 9/00885
USPC ...................................... 340/539.12
See application file for complete search history.

(56) References Cited

U.S. PATENT DOCUMENTS

| | | | |
|---|---|---|---|
| 8,284,068 B2* | 10/2012 | Johnson ................. | G08B 21/24 340/568.1 |
| 9,345,645 B1* | 5/2016 | Chernyak ............. | A61J 7/0084 |
| 2005/0252924 A1* | 11/2005 | Pieper ................... | A61J 7/0481 221/25 |
| 2014/0379874 A1 | 12/2014 | Starr et al. | |
| 2015/0257981 A1 | 9/2015 | Arad et al. | |
| 2016/0212389 A1 | 7/2016 | Mehrotra et al. | |

(Continued)

FOREIGN PATENT DOCUMENTS

WO    2018/224460 A1    12/2018

OTHER PUBLICATIONS

International Search Report, PCT/US2020/61829 (dated Feb. 11, 2021) (2 pages).

*Primary Examiner* — Mark S Rushing
(74) *Attorney, Agent, or Firm* — McDonnell Boehnen Hulbert & Berghoff LLP

(57) ABSTRACT

An electronic device, method of use, and system for improving medication compliance are disclosed. The device may comprise an upper cover configured to adhere to a pill bottle cap; a printed circuit board (PCB); a battery communicatively linked to the PCB; a sensor communicatively linked to the PCB; and a lower cover through which the sensor is configured to transmit and receive signals.

20 Claims, 3 Drawing Sheets

(56) References Cited

U.S. PATENT DOCUMENTS

2016/0324726 A1* 11/2016 Roberts .................... A61J 7/04
2017/0351838 A1    12/2017 Chen et al.

* cited by examiner

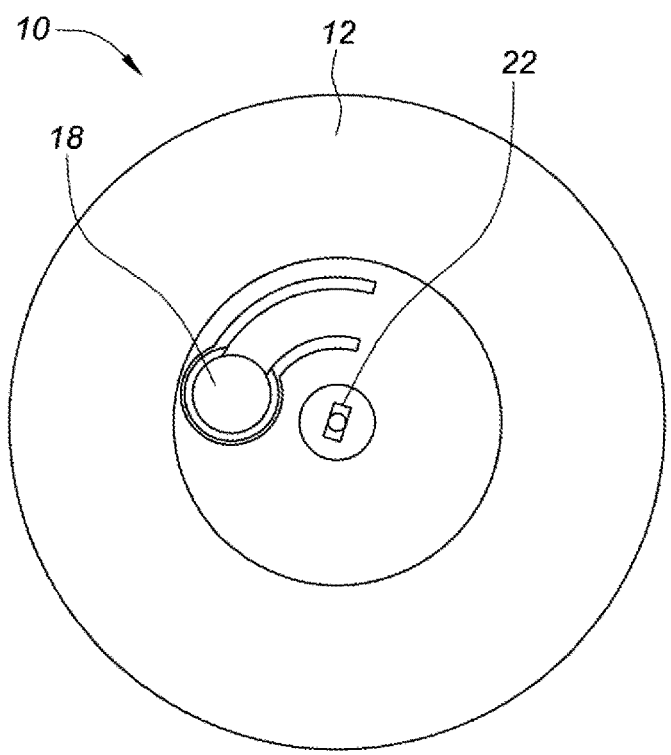
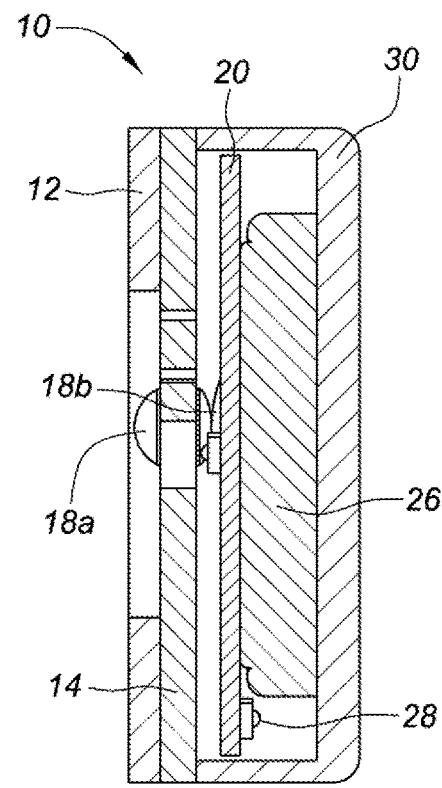
FIG. 2
FIG. 4
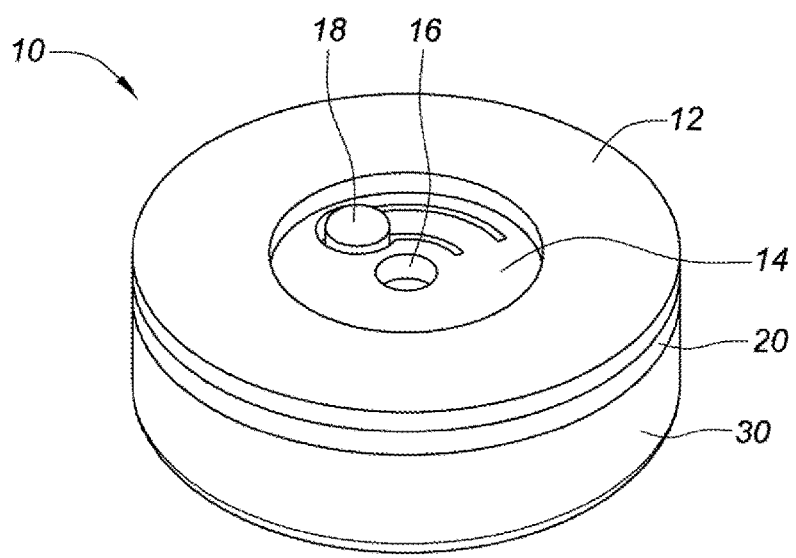
FIG. 3

ELECTRONIC PILL BOTTLE TAG

CROSS-REFERENCE TO RELATED APPLICATIONS

This application claims the benefit of U.S. provisional application No. 62/938,757 filed 21 Nov. 2019, which is hereby incorporated by reference as though fully set forth herein.

BACKGROUND a. Field

The instant disclosure relates to a device and method for improving medication compliance. In one embodiment, the instant disclosure relates to a device and method for providing medication compliance data to patients, caregivers, relatives, and/or health care professionals.

b. Background Art

Medication noncompliance has been a longstanding, highly significant, and often costly issue in the prescription, over-the-counter (OTC), and supplement industries. Although noncompliance is huge concern in the elderly population, it can be a hurdle for patients of all ages, socioeconomic groups, education levels, etc.

Existing solutions to medication noncompliance often require custom hardware or pill-dispensing bottles. Pill dispenser systems, pill lock boxes, and smart "day of the week" pill reminder systems are a few examples of such existing solutions. These solutions have not been widely adopted due to increased costs, lack of "ease of use," and additional challenges (e.g., transferring pills out of their original container could mean losing important medical, legal, and personal information). Thus, there is a need for a low-cost, low-power, easy-to-use device that can be used with original/standard pill bottles to improve medication compliance.

The foregoing discussion is intended only to illustrate the present field and should not be taken as a disavowal of claim scope.

BRIEF DESCRIPTION OF THE DRAWINGS

FIG. 2 is a bottom view of the electronic pill bottle tag shown in FIG. 1.

FIG. 3 is a bottom, perspective view of the electronic pill bottle tag shown in FIG. 1.

FIG. 4 is a cross-sectional, side view of the electronic pill bottle tag shown in FIG. 1.

DETAILED DESCRIPTION OF EMBODIMENTS

Figure 1:
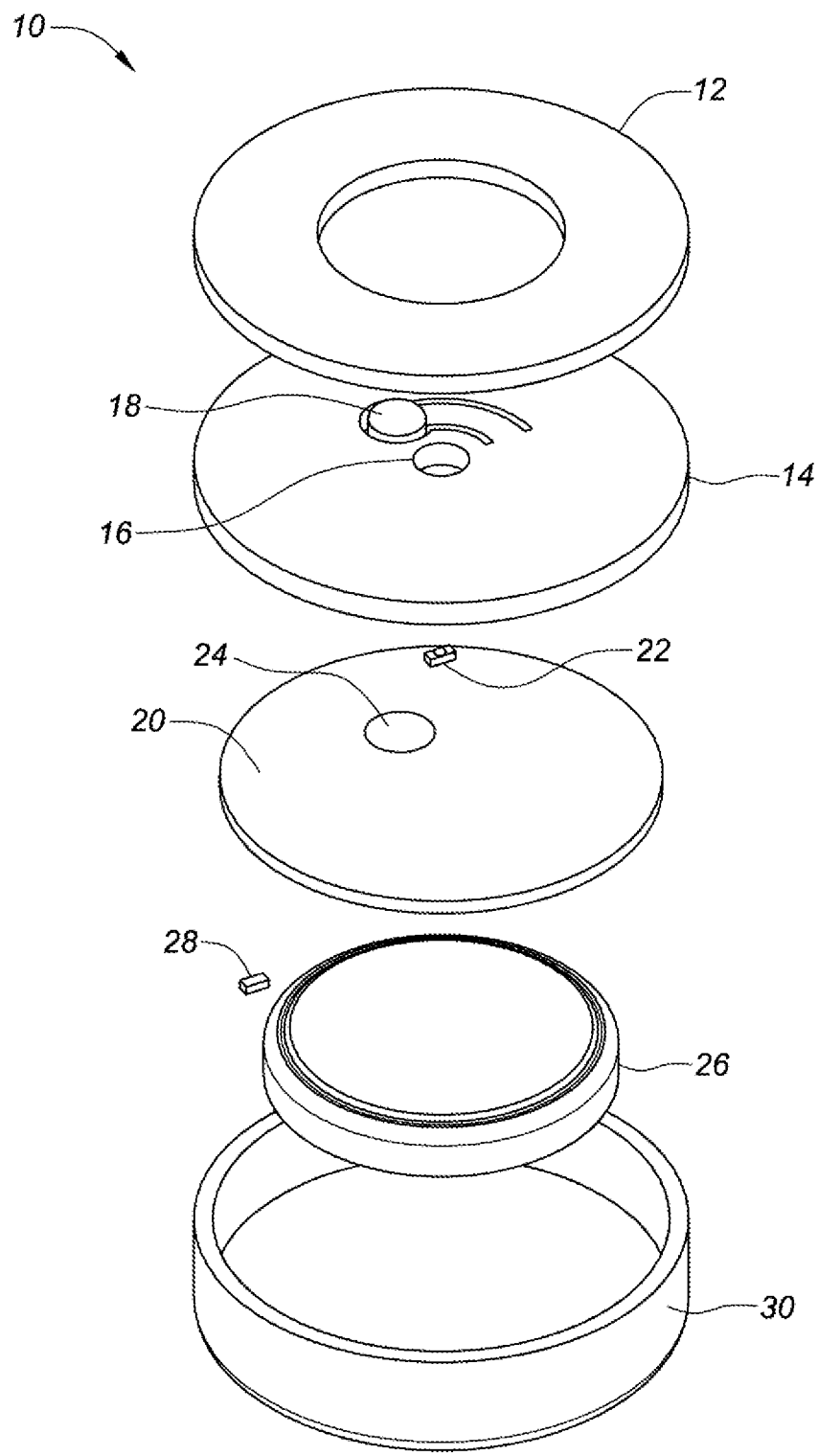
FIG. 1 is an exploded view of an example of an electronic pill bottle tag, in accordance with the embodiments described herein.

Several embodiments of a low-cost, low-power, disposable device or "tag" that can be used to notify users when to take their medication are disclosed herein. The tag can be attached to an original or standard pill bottle or pill bottle lid via an adhesive, for example. Alternatively, the tag can be attached to a custom manufactured or tooled model of a pill bottle or lid. The tag can be battery-operated and can include low-power wireless technology (e.g., bluetooth) to send notifications to a user's phone, a user's computer, an application, a kiosk, a wireless communication network (e.g., LAN, WAN, Internet, intranet, Wi-Fi network, Bluetooth network, cellular network and/or the like), or other connected device indicating that a pill bottle has been opened. The tag can detect when the bottle has been opened using optical, acoustic, haptic, or other technology in order to "assume" a pill has been taken. The tag can also send notifications or prompts to the user when a pill has been missed. Further, the tag can connect to a software suite and provide nationwide monitoring of usage statistics for improved market/advertising feedback for specific drugs.

Referring to FIGS. 1-5B, the device or tag 10 can be a small electronic device configured to be attached to any bottle cap with an adhesive or double-sided tape, glue, or a magnet, for example. The circular adhesive ring 12 can be configured to attach to the underside of the cap of a pill bottle (e.g., a prescription medication, an over-the-counter medication, or a supplement). Alternatively, the adhesive ring 12 could be attached to the top of the cap or to the interior or exterior of the bottle, or simply placed inside of the pill bottle (without attachment). The adhesive ring 12 can further be attached to a circular upper cover 14 via standard manufacturing techniques (e.g., glue, welding, screws, solder). The circular upper cover 14 can include a centrally located hole 16 and a function button 18, which in turn can be attached to a printed circuit board (PCB) 20. The PCB 20 can include a light emitting diode (LED) indicator 22 configured to shine light up through the centrally located hole 16. Although shown on the periphery of the PCB 20, the LED indicator 22 can be located anywhere on or within the PCB 20. The PCB 20 can also include a contact pad 24 for the function button 18. The PCB 20 is further attached (again, via standard manufacturing techniques) to a battery 26, such as a lithium battery, and to an optical sensor 28, such as an infrared (IR) transmitter/receiver, for detecting when a pill bottle is opened. Finally, a lower cover 30 through which the sensor detects a bottle opening event can be attached to the underside of the battery 26. The lower cover 30 may be transparent to the optical sensor/receiver 28.

Figure 5A:
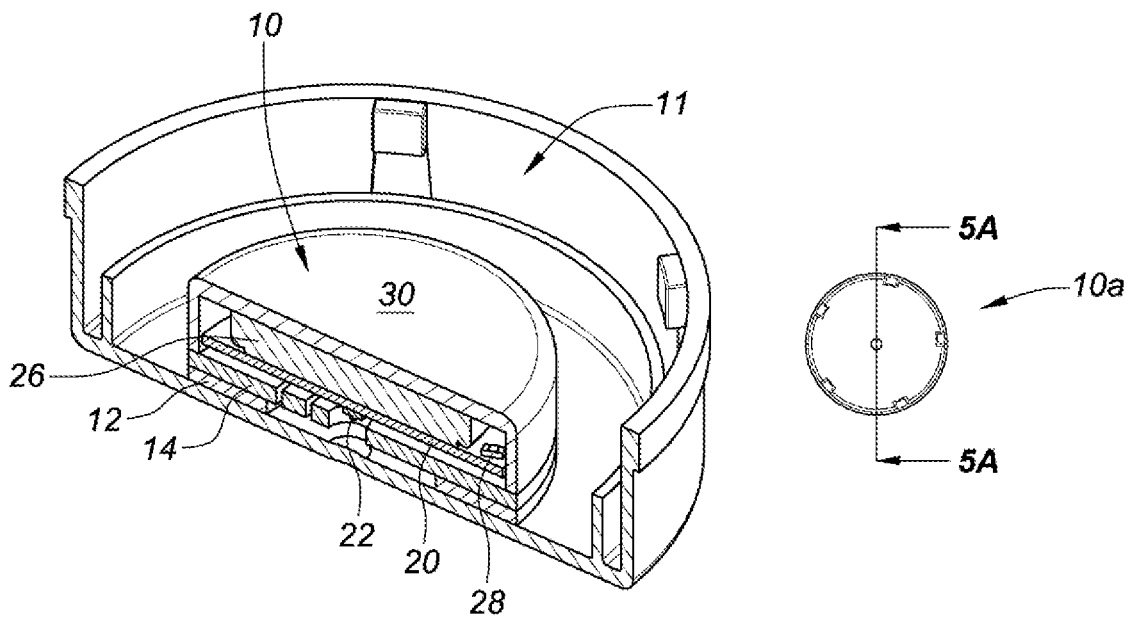
FIG. 5A is a cross-sectional, perspective view of the interior of one embodiment of an electronic pill bottle tag.

Once the device or tag 10 is adhered to the underside of a pill bottle cap or lid, several different methods can be used to detect when the bottle is opened. In one embodiment, optical sensor 28 (i.e., the optical transmitter and the optical receiver) can be angled straight down towards the bottom of the bottle. This embodiment is shown in FIG. 5A, which is a cross-sectional view along line 5A-5A of tag 10a. The optical transmitter can be configured to pulse IR light signals and the optical receiver can be configured to measure the strength of the return signal in order to determine the distance traveled by the signal and/or depth of the bottle. If the lid is attached the bottle, the signal will reflect off the bottom of the bottle or the pills contained within the bottle, and the return signal detected by the optical receiver will be relatively strong. If the lid is not attached to the bottle, the return signal detected by the optical receiver will be relatively weak and suggestive of an "infinite" field beyond the depth of a typical bottle. Alternatively, an ultrasound transducer and receiver can be used in place of the optical transmitter and receiver, respectively, and ultrasound signals can be used in place of IR light signals to detect whether the lid is attached to the bottle.

Figure 5B:
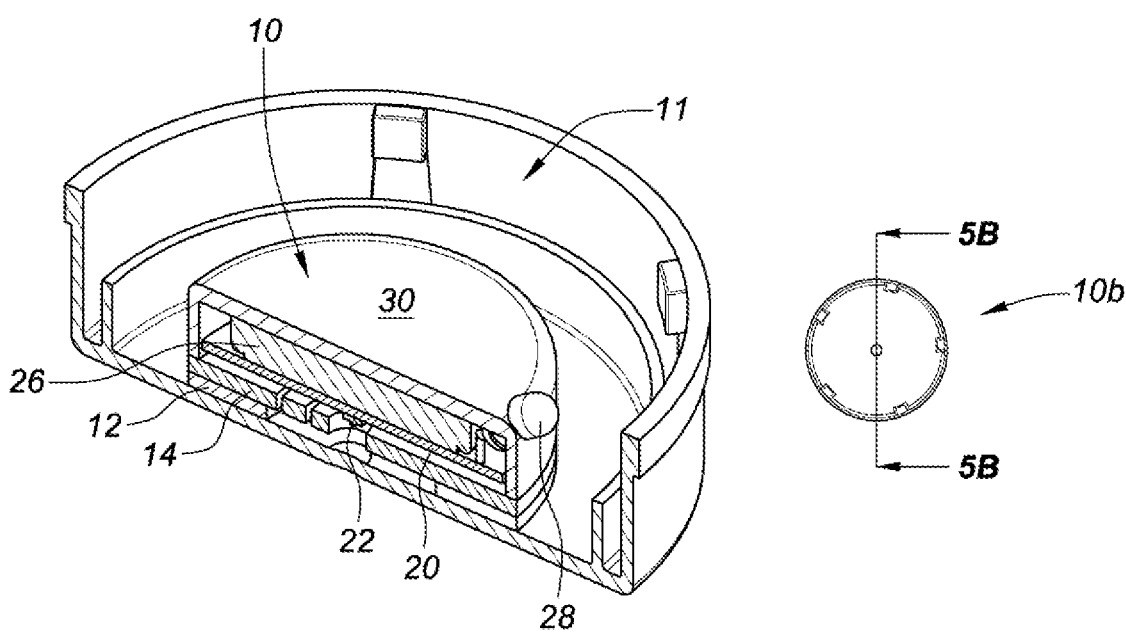
FIG. 5B is a cross-sectional, perspective view of the interior of another embodiment of an electronic pill bottle tag.

In another embodiment, the optical sensor 28, including the optical transmitter (or ultrasound transducer) and the optical (or ultrasound) sensor, can be protruded into the bottle slightly and at a right angle. This embodiment is shown in FIG. 5B, which is a cross-sectional view along line 5B-5B of tag 10b. The protruded and angled orientation of the sensor 28 allows for detection of a return signal reflected from the side of the lid (as opposed to the bottom of the bottle or the pills occupying the bottle) when the lid is attached to the bottle. Although only one sensor 28 is shown, multiple sensors could protrude into the bottle at various points along the circumference of the lower cover 30.

In another embodiment, optical time of flight (e.g., as determined by a time-of-flight laser-ranging sensor) can be used to detect whether or not the bottle lid is attached to the bottle. This method would allow for increased accuracy, and may also be associated with an increased cost. Instead of simply detecting "lid open or closed," however, this technology could allow for detection of the approximate number of pills left in the bottle.

In yet another embodiment, a mechanical switch (e.g., the function button 18 shown in FIGS. 1-4), can be used in place of an IR light or ultrasound signal to detect whether the lid is on the bottle. As shown in FIG. 4, the mechanical switch can include an actuator part 18a and a PCB-mounted button pad 18b. When the lid is attached, the mechanical switch will be activated due to the force of the lid on the bottle (e.g., the actuator part 18a will depress the button pad 18b). This force may be provided via a spring mechanism, for example, and communicated via the PCB 20 to a user's phone, computer, or other device. Activation of the mechanical switch can also cause an electrical signal to be sent to the PCB 20, such as a wake up signal (e.g., signaling the tag to switch from a low-power shipping mode to a higher-power active mode) or a signal triggering initiation of a wireless connection with a user's phone, computer, or other device. The mechanical switch may be integrated into the tag itself, and may be activated when a user firmly pushes the tag against the lid, such as by using a foam version of the adhesive material 12 as a sort of spring or sponge force that the user must press against in order to active the switch.

In yet another embodiment, an inductive or capacitive sensor located on or within the lid tag can be used to detect a metallic label or object that is adhered to the bottle. A determination of whether the lid is attached to the bottle can then be made based on the inductive or capacitive strength. A stronger (or weaker) signal will be suggestive of a closer (or farther) distance of the lid from the bottle.

The LED indicator 22 can be configured to shine down into the bottle to illuminate the bottle when it is time for a user to take a pill or when a dose has been missed. Different colors can be used to indicate an upcoming versus missed dosage. Further, a full RGB LED can be used to allow users to configure different colors for different medications. Similarly the user could configure the flashing pattern or rate as desired. A flashing pattern with a relatively slow rate may be advantageous for conserving the battery 26 used to power the LED 22. In addition, the LED indicator 22 can be configured to not shine at all if bottle opening has been detected (e.g., by an optical, ultrasound, radiofrequency, inductive or capacitive sensor)

In an embodiment, the tag 10 can be configured to automatically increase or decrease one or more of the following based on a user's prescription dosage lifetime (e.g., when pills should run out): (i) the duty cycle of the LED, (ii) how long before the dosage window to flash, (iii) the frequency of lid removal detection sampling intervals (e.g., to maximize detection accuracy), and (iv) wireless communication intervals and strength (e.g., for improved interaction with a user's phone, computer, or other application). The goal would be to use the full energy in the battery at around the time the prescription should be finished, yet provide the optimal user experience, since many tradeoffs must often be made to conserve battery. For example, without knowing a prescription time frame, the tag may need to conserve battery for the worst case requirement (e.g., 3 months), as opposed to a single prescription (e.g., 2 weeks), and as a result the LED could potentially shine more brightly or for longer time periods during notifications. In this case, it is assumed that the tag is disposable; thus, there would be no reason to have any battery capacity left after the dosage lifetime is finished. The battery of the disposable tag would be non-replaceable and intended to be disposed along with the tag itself, thereby minimizing the size and cost of the overall tag. In alternative embodiments, the battery may be rechargeable and/or replaceable.

As mentioned above, the device or tag 10 can be configured to use wireless communication (e.g., bluetooth or other low power radio frequency signals) to connect to a user's phone or other device. The location of the tag 10 and/or the user device with which it communicates can be tracked via GPS and/or an application on the user device. As an alternative to Bluetooth or other low power RF wireless, the dosing schedule could be sent to the tag 10 (e.g., to the PCB 20) using IR or other light emitting methods. The same optical transmitter/receiver 28 that is used for lid detection could be used to provide the dosing schedule to the tag. Alternatively, a separate bluetooth to IR device could be created to communicate with and configure the tags. For example, a plurality of low cost tags could be configured with one bluetooth or IR device. A tag may also have a QR code or other unique barcode on or attached to it to allow a user's phone app (or, e.g., a kiosk device) to quickly scan and identify the tag prior to configuration or programming (e.g., when a user has multiple tags for multiple medication bottles). Manufacturers can provide unique tag identifications which automatically register from kiosk to kiosk, for example, to better track the flow of bottles and to prevent counterfeit activity. Once configured, the tag can communicate with the phone app or kiosk and report when bottle opening has been detected (which may be assumed to represent a completed dose). Moreover, the LED indicator on the tags can be configured to light up or flash at a high speed during or immediately after configuration, or upon user request from an application, to help the user locate or identify which tag is being configured and/or should be adhered to the bottle.

An phone app or other application can use wireless and/or other communication methods to send a configuration to the tag—e.g., what color of light to shine when it is time for a user to take a dose of medication, how soon to shine before the dosing window, and what color to shine when a dose has been missed. In some embodiments, tags can be paired using an encrypted key with a central keystore to provide notification of unauthorized use. In some embodiments, the application can include optical character recognition (OCR) scanning technology to recognize a user's prescription and then automatically determine, store, and/or send dosage interval information to the tag. The application can further be configured to receive dosage interval information from an external database (e.g., credentialed internet sites), as well as to allow a user to select and/or confirm typical dosing schedules for a given medication. Alternatively, the application can be configured to receive dosing information from a QR code or other camera/phone readable barcode or identifier printed on the bottle label, sales receipt, or kiosk screen, for example. The application can further be configured to send dosing information or other configuration settings directly to the tag (e.g., so as to run independently from a user's phone). The application can include user account passwords. Further, the application can allow pharmacies to send configuration information to a tag, as well as push notifications when it is time for a user to take a dosage or refill a prescription, for example. The application can also be configured to aggregate nationwide usage data, which may be used to help analyze the effects of marketing and usage programs.

In addition to the above-described application, software running on computers, kiosks, or other devices at the point of sale (POS) of the prescription/bottle could be used to configure the dosing schedule on a tag at the same time the prescription is filled and given to the user. A USB to Bluetooth or IR device can also be provided to allow POS kiosks and application software to configure the tags (e.g., if the hardware is not already available on the POS kiosk or computer). A standalone POS hardware device can also be provided to pharmacies, kiosk computers, or other large volume users, allowing for the incorporation of any or all application features. This may be useful in the event that integrating directly into the point of sale kiosk software is not practical. A standalone "gateway" for end users can be used to replace some or all the functionality of the phone application, for example. A software library can be provided to program specific tags to allow existing third party dosing schedule apps, or other software (e.g. POS software used at the pharmacy) to easily integrate with and configure the tags. Further, a software program can be configured to visualize utilization and use across the nation via location meta data from Bluetooth phone pairing.

In an embodiment, a paired "lockout" tag corresponding to a given tag can be provided to children or adhered to an item of clothing typically worn by a child or an authorized user. An alarm or alert may be provided if the bottle is opened and the lockout tag (and therefore the child or authorized user) is within some disallowed proximity to the bottle. This can be used as a tool to stop accidental overdoses by children or enforce various authorization and tracking protocols (e.g., for controlled substances).

To maintain low power, tags may ship in a low power "off" or "shelf-life" mode until woken up for the first time by user interaction. One or more of the following techniques can be used for such a wake up event, as well as for other user interaction/identification purposes. For example, capacitive button technology can be used to detect a human hand or finger through the lid and during tag application process. In another example, a mechanical/physical button can be exposed in a gap/cutaway of the adhesive (e.g., adhesive ring 12). The user must either press this, or alternately, the act of sticking to a lid can trigger the physical button. Additionally, the adhesive backing material (the non-sticky part) can be configured to hold down the button and when the backing is removed, the button is released, waking up the tag. The backing material may also be a metallic foil and a small inductive distance or capacitive sensor could be configured to detect the lack of metallic foil (i.e., when the backing is removed).

To further conserve power consumption, a method can be used to detect human interaction or other requisite events before the lid is removed so that the higher operating power modes are only be used when a lid removal event is likely. As an example, when the user is detected to have touched the bottle, the light indicator (e.g., LED indicator 22) could turn brighter or flash longer. Alternatively, wireless communication could be enabled in a higher power mode only for a certain time interval after the user has been detected touching/moving the tag. Detection of user interaction may include use of a capacitive sensor embedded into the tag to detect a hand on top of the lid. Detection of user interaction may also involve use of an accelerometer to detect movement (i.e., the movement of the lid being opened).

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electronic pill bottle tag device comprising:
   an upper cover configured to adhere to a pill bottle cap;
   a printed circuit board (PCB) including a function button formed as part of a mechanical spring within the PCB;
   a battery communicatively linked to the PCB;
   a sensor communicatively linked to the PCB; and
   a lower cover through which the sensor is configured to transmit and receive signals.

2. The device of claim 1, further comprising a light emitting diode (LED) indicator located on or within the PCB, the LED configured ot emit light through at least one of the upper cover and the lower cover.

3. The device of claim 1, wherein the sensor is an optical sensor comprising a transmitter configured to emit an initial light signal and a receiver configured to receive a return light signal, and wherein a reflection of the initial light signal produces the return light signal.

4. The device of claim 3, wherein the receiver is configured to measure at least one of a magnitude or a time of the return light signal.

5. The device of claim 1, wherein a mechanical switch is configured to be force activated through the upper cover.

6. The device of claim 5, wherein the mechanical switch is further configured to electronically communicate with the PCB.

7. The device of claim 1, wherein the sensor is a wireless communication sensor.

8. The device of claim 1, further comprising a location tracking device or application.

9. The device of claim 1, further comprising a barcode or QR code configured to be scanned and identified by a user device or a kiosk device.

10. The device of claim 1, wherein the battery is configured of operate ni a low-power mode and in a high-power mode.

11. The device of claim 1, wherein the sensor comprises at least one of an optical sensor, an ultrasound sensor, a radio frequency sensor, an inductive sensor, and a capacitive sensor.

12. A system for improving medication compliance comprising
   a bottle cap; and
   an electronic bottle cap tag, the tag comprising:
      an upper cover configured to adhere to the bottle cap;
      a printed circuit board (PCB) including a function button formed as part of a mechanical spring within the PCB;
      a battery communicatively linked to the PCB;
      a sensor communicatively linked to the PCB; and
      a lower cover through which the sensor is configured to transmit and receive signals.

13. The system of claim 12, wherein the bottle cap comprises are movable covering for a bottle holding at least one of a prescription medication, an over-the-counter medication, or a supplement.

14. The system of claim 12, wherein the electronic bottle cap tag is disposable.

15. The system of claim 12, wherein the electronic bottle cap tag is configured to detect removal of the bottle cap from a bottle.

16. The system of claim 12, wherein the electronic bottle cap tag is configured to wirelessly communicate with an external network or user device.

17. The system of claim 12, wherein the sensor comprises at least one of an optical sensor, an ultrasound sensor, a radio frequency sensor, an inductive sensor, and a capacitive sensor.

18. A method for improving medication compliance comprising:
   affixing an electronic bottle cap tag to a medication bottle cap;
   detecting a removal of the medication bottle cap from a corresponding medication bottle based on a signal detected by the electronic bottle cap tag, the signal being at least one of an optical signal, an ultrasound signal, a radiofrequency signal, an inductive signal, or a capacitive signal;
   communicating the detected removal to a printed circuit board (PCB) of the electronic bottle cap tag, wherein the PCB includes a function button formed as part of a mechanical spring within the PCB; and
   communicating the detected removal to at least one of an application, a wireless communication network, a phone, a computer, a kiosk, or an external user device.

19. The method of claim 18, further comprising:
   collecting removal data, the removal data comprising at least one of a time of the detected
   removal, a frequency of the detected removal, or a failure to detect the removal;
   configuring an LED indicator based on the removal data;
   wherein the electronic bottle cap tag comprises the LED indicator.

20. The method of claim 19, wherein configuring the LED indicator comprises configuring at least one of a timing or a frequency of light emitted by the LED.

* * * * *